United States Patent [19]

Chazov et al.

[11] 4,446,316

[45] May 1, 1984

[54] DEXTRAN DERIVATIVE OF FIBRINOLYSIN

[75] Inventors: Evgeny I. Chazov; Vladimir N. Smirnov; Vladimir P. Torchilin, all of Moscow; Igor M. Tereshin; Boris V. Moskvichev, both of Leningrad; Grigory M. Grinberg, Moscow; Agris Z. Skuya; Gersh I. Kleiner, both of Riga, all of U.S.S.R.

[73] Assignee: Vsesojuzny Kardiologichesky Nauchny Tsentr, Moscow, U.S.S.R.

[21] Appl. No.: 329,025

[22] Filed: Dec. 9, 1981

[30] Foreign Application Priority Data

Dec. 31, 1980 [SU] U.S.S.R. ............................... 3230869

[51] Int. Cl.³ ............................................. C08B 37/02
[52] U.S. Cl. .................................... 536/112; 424/180
[58] Field of Search ......................................... 536/112

[56] References Cited

U.S. PATENT DOCUMENTS 4,020,268 4/1977 Nishikawa et al. ................. 536/112
4,264,766 4/1981 Fischer ................................ 536/112

FOREIGN PATENT DOCUMENTS 833985 6/1979 U.S.S.R. ............................... 536/112

OTHER PUBLICATIONS

Carlin et al., "Chem. Abst.", vol. 93, 1980, pp. 218,705(a). 191,171(P).
Carlin et al., "Chem. Ast.", vol. 93, 1980, pp. 218,705(a).
Katsuda et al., "Chem. Abst.", vol. 94, 1981, p. 176(c).
Kardiologiya, Moscow, 1977, No. II, pp. 139-142.

*Primary Examiner*—Johnnie R. Brown
*Attorney, Agent, or Firm*—Robert E. Burns; Emmanuel J. Lobato; Bruce L. Adams

[57] ABSTRACT

A method of preparing a polysaccharide derivative of fibrinolysin which comprises reacting fibrinolysin with dextran dialdehyde having a molecular mass of from 20,000 to 110,000 at a pH of from 8.0 to 9.5 and at a temperature within the range of from 5° to 30° C. with the formation of a covalent bond; the resulting fibrinolysin derivative is reduced with sodium borohydride and isolated.

5 Claims, No Drawings

DEXTRAN DERIVATIVE OF FIBRINOLYSIN

BACKGROUND OF THE INVENTION

The present invention relates to the chemical and pharmaceutical industry, and more particularly, to a method for preparing a polysaccharide derivative of fibrinolysin, having a prolonged thrombolytic activity and fit for use in medicine.

Fibrinolysin finds extensive application in medicine as a thrombolytic preparation in the therapy of such diseases as myocardial infarction, thromboses and thromboembolism of lung arteries. The preparation is administered intravenously during several days. However, the fibrinolysin therapy is made complicated by the following factors. First, fibrinolysin does not have substrate specificity. It hydrolyzes not only fibrin, but other proteins as well, such as fibrinogen, casein and some proteins of the blood clotting system. Secondly, the application of fibrinolysin may cause not only an increase in the fibrinolytic activity, but also activation of the clotting system: as a result, secondary origination of clots may take place. Thirdly, as all enzymatic preparations, fibrinolysin becomes rapidly inactivated under physiological conditions due to the effect of pH, temperature, endogenous proteases and natural inhibitors; it is rapidly brought out of the blood flow so that it becomes necessary to introduce large doses of the enzyme during a long period of time. Moreover, treatment of patients with blood clots of considerable dimensions and with low anticoagulant characteristics of the blood proved to be unsuccessful.

Methods are known in the art for bonding enzymes by polymers which allow the attainment of preparations which, compared with native enzymes, have an essentially higher stability to various inactivating factors, longer residence in the organism and lower antigenicity. Thus, a method is known for preparing a derivative of fibrinolysin by covalently bonding fibrinolysin with a copolymer of ethylene and maleic anhydride at a temperature of from 0° to 4° C. over several hours. The resulting products have a biological activity of 15 to 30% (Zeitschrift für Analytische Chemie, 1968, Band 243, No. 2, S.457).

The fibrinolysin derivative prepared by this method is incompatible with the tissues of the living organism, since the copolymer of ethylene with maleic anhydride is not biodegradable and cannot find application is medical practice.

Also known is a method of preparing a derivative of fibrinolysin with an aldehyde-containing polysaccharide which involves the reaction of fibrinolysin with a modified aldehyde-containing sephadex in a phosphate buffer at the temperature of 4° C. during several hours. The non-bonded enzyme is washed-out by successive washings with a glacial phosphate buffer, 0.001 N solution of hydrochloric acid, 1 M solution of sodium chloride, with water and with a mixture of water and acetone, whereafter the preparation is dried with acetone (Kardiologiya, Moscow, 1977, No. 11, pp. 139–142).

The compound prepared by the above method is not soluble in water and aqueous solutions, this circumstance limiting its applicability for medical purposes.

SUMMARY OF THE INVENTION

It is an object of the present invention to provide a method of preparing a polysaccharide derivative of fibrinolysin which ensures the attainment of a water-soluble derivative of fibrinolysin having a high thrombolytic activity of prolonged action, stability under physiological conditions and suitability for application in medicine.

This object is accomplished by the method for preparing a polysaccharide derivative of fibrinolysin comprising the interaction of fibrinolysin with an aldehyde-containing polysaccharide with the formation of a covalent bond and subsequent isolation of the desired product. According to the present invention as the aldehyde-containing polysaccharide use is made of dextran dialdehyde with a molecular mass of from 20,000 to 110,000; the process is conducted at pH of from 8.0 to 9.5 and temperature of from 5° to 30° C.; the resulting polysaccharide derivative of fibrinolysin, prior to isolation thereof, is additionally reduced with sodium borohydride. Sodium borohydride is preferably taken in a ratio to the polysaccharide derivative of fibrinolysin of 1.5–2.0:1 respectively.

The resulting polysaccharide derivative of fibrinolysin has thrombolytic activity, increased stability and an extended time of circulation in the organism.

DESCRIPTION OF THE INVENTION

The schematic structure of the product can be represented as follows:

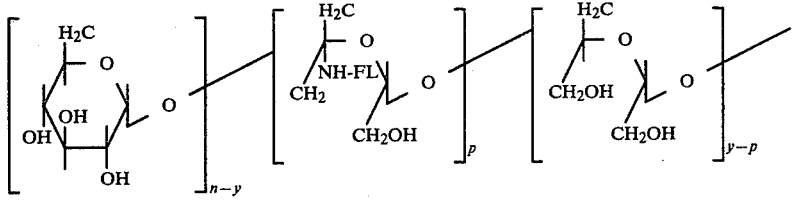

wherein FL is fibrinolysin, n-100% (molar) glucopyranose units of dextran, y-10–25 molar % of oxidized glucopyranose units of dextran, p-molar percentage of NH$_2$ groups of fibrinolysin participating in bonding. The content of protein in the preparation is 10 to 30%, the content of dextran-90–70%.

The resulting polysaccharide derivative of fibrinolysin was experimentally studied in animals to evaluate its thrombolytic activity, prolonged action and toxicity.

The study of the specific (thrombolytic) effect of the polysaccharide fibrinolysin derivative according to the present invention has been studied on models of thromboses of a rabbit's jugular vein and a dog's femoral vein or artery. Thrombi of 1 to 2.5 cm size were formed in the above-mentioned animals which fully obliterated the cross-section of a blood vessel. The administration of the test preparation at the background of heparin was started one hour after the thrombus formation.

On the basis of an expected prolonged fibrinolytic effect of the preparation according to the present invention, a test dose of the preparation ranging from 400 to 4,000 units per kg of the bodyweight is dissolved in a physiological solution, 20–30 ml for rabbits and 50–100 ml for dogs, and injected by means of a syringe in a jet-like manner intravenously over 20 minutes, not following the instruction on the use of fibrinolysin (intravenously by the dropwise method at a rate of 10–12 drops per minute).

The dynamics of the thrombus formation and lysis was observed visually and by palpation during 6 hours of the experiment, after one, two and three days. The angiography and fluorometry were carried out prior to the beginning of the treatment and one day after the administration of the preparation.

The results showing thrombolytic activity of the polysaccharide derivative of fibrinolysin are given in Table 1.

TABLE 1

| Group of animals 1 | Test preparation 2 | Number of animals 3 | Dose of preparation per kg of bodyweight, units 4 | Efficiency of the therapy (lysis of thrombus) 5 |
|---|---|---|---|---|
| Rabbits | Fibrinolysin | 1 | 600 | no lysis |
| Rabbits | Fibrinolysin | 2 | 800 | full lysis |
| | | 1 | 800 | no lysis |
| | | 1 | 1,200 | full lysis |
| | | 1 | 2,000 | full lysis |
| | | 1 | 4,000 | full lysis (died from hemorrage |
| | Fibrinolysin derivative of the invention | 7 | 400 | full lysis |
| | | 1 | 600 | full lysis |
| Dogs | Fibrinolysin | 1 (femoral vein) | 800 | no lysis |
| | | 1 (femoral vein) | 800 | no lysis |
| | | 1 (femoral vein) | 1,600 | full lysis |
| | | 1 (femoral vein) | 1,600 | full lysis |
| | Fibrinolysin derivative according to the present invention | 3 (femoral vein) | 600 | full lysis |
| | | 3 (femoral vein) | 600 | full lysis |

It follows from the experimental data that the fibrinolysin therapy of rabbits gives no thrombolytic effect in all cases of administration of the minimal treating dose (800 units per kg). There are observed bleeding, pathological changes in the third phase of blood coagulation, drop of the content of fibrinogen during the first hours after administration down to zero. Increasing the dose to 4,000 units/kg causes death of animals from fibrinolysin. In contrast to the native fibrinolysin, the treatment with the fibrinolysin derivative according to the present invention is more effective even at the minimal therapeutical dose of 400 units/kg. Furthermore, the fibrinolytic effect of the fibrinolysin derivative according to the present invention is observed for a longer period—up to two days after administration. The preparation causes no sharp changes in the third phase of blood coagulation, wherein the treatment is not accompanied by bleeding. The results obtained on dogs have proven the regularities of the thrombolytic therapy established on rabbits.

The fibrinolytic effect ensured by the fibrinolysin derivative according to the present invention is observed also on the second day after introduction of the preparation into the animal's organism, whereas upon administration of native fibrinolysin the duration of the effect is limited to one day. The prolonged effect of the fibrinolysin derivative according to the present invention has been studied in experiments on dogs in comparison with the effect of native fibrinolysin. The test results are summarized in Tables 2 and 3 hereinbelow.

TABLE 2

Variation of lysis duration (in minutes) of the euglobulin fraction of dog's plasma with experimental thrombosis upon administration of the fibrinolysin derivative according to the present invention and native fibrinolysin

| Preparation 1 | Number of animals 2 | Initial parameter 3 | Test duration | | |
| | | | after 2 hours 4 | after 1 day 5 | after 2 days 6 |
|---|---|---|---|---|---|
| Preparation of the invention | 6 | 70 | 90 | 1 | 10 |
| Native fibrinolysin | 4 | 38 | 3 | 105 | 90 |

TABLE 3

Variation of thrombin time (in seconds) in dogs with experimental thrombosis after administration of the fibrinolysin derivative according to the present invention and native fibrinolysin

| Preparation | Number of animals | Initial parameter | Test duration after administration of the preparation | | |
| | | | after 2 hours | after 1 day | after 2 days |
|---|---|---|---|---|---|
| Preparation of the invention | 6 | 35 | 90 | 92 | 210 |
| Native fibrinolysin | 4 | 22 | 195 | 95 | 97 |

The toxicity of the fibrinolysin derivative according to the present invention was studied on white mice, rats, rabbits and dogs. The test results are shown in Table 4. The results obtained show that $LD_{50}$ of different lots of the fibrinolysin derivative according to the present invention varies within the relatively narrow range of from 5,000 to 6,000 units/kg. The toxicity of the fibrinolysin derivative according to the present invention has turned out to be similar to that of native fibrinolysin. A single administration of the fibrinolysin derivative of the present invention to the animals in doses exceeding, by 4–5 times, the therapeutic dose, does not result in their death. In the test doses the preparation shows no injuring effect on the vessels and causes no macro- and microscopic changes in the inner organs. In therapeutical doses it has no effect on the central nervous system and blood pressure.

TABLE 4

Toxicity of the fibrinolysin derivative of the invention for animals of different species upon intravenous injection

| Animal species | Number of animals | Doses, un/kg and test results | | | | | | | | LD$_{50}$ un./kg |
|---|---|---|---|---|---|---|---|---|---|---|
| | | 500 | 1000 | 1500 | 2000 | 2500 | 3750 | 5000 | 6250 | |
| Mice | 34 | | | | 0/6 | 0/6 | 1/5 | 2/4 | 6/0 | 5000 |
| Rats | 30 | | | | 0/6 | 0/6 | 2/4 | 3/3 | 6/0 | 4586 |
| Rabbits | 30 | 0/6 | 1/5 | 2/4 | 2/4 | 6/0 | | | | 1834 |
| Dogs | 7 | 0/3 | 0/3 | 0/1 | | | | | | — |

The test results shown hereinabove show that:

1. The treatment of experimental thrombosis by the method of a single intravenous jet-like infusion of the preparation according to the present invention is effective at the minimal dose of 400 units/kg of the bodyweight, whereas the minimal therapeutic dose of native fibrinolysin equal to 800 units/kg of the bodyweight does not always cause the lysis of a thrombus.

2. Normalization of changes in the blood clotting system caused by the administration of the fibrinolysin derivative according to the present invention occurs in the test animals on the second day which demonstrates prolongation of the effect ensured by the preparation by 2-3 times as compared to native fibrinolysin.

3. The preparation of the present invention causes no sharp changes in the third phase of blood coagulation and, hence, makes it possible to avoid bleedings which frequently occur in the case of application of fibrinolytics.

4. The fibrinolysin derivative according to the present invention has a low toxicity. An intravenous injection of the preparation in doses, exceeding by 4-5 times the therapeutical one, does not result in death of animals.

The use of fibrinolysin derivative according to the present invention possessing a prolonged effect makes it possible to replace the many-day intravenous drop-wise method of introduction of the preparation by the single-time intravenous jet-like method, reduce the course dose and thus lower the number of complications, simultaneously with increasing efficiency of the thrombolytic therapy.

The fibrinolysin derivative according to the present invention can be employed for the therapy of acute thromboembolism and thromboses of pulmonic arteries (prior to the development of gangrene), thrombophlebitis, thrombosis of peripheral veins, acute myocardiac infarction, thrombosis of the central vein or artery of the eye retina.

The process for the preparation of the polysaccharide derivative of fibrinolysin according to the present invention is effected in the following manner.

Dextran dialdehyde with a molecular mass of from 20,000 to 110,000 is prepared by any conventional method by oxidation of dextran to aldehyde groups in the glucopyranose unit, e.g. by oxidation of dextran with iodic acid or its potassium salt. A solution of fibrinolysin is added to dextran dialdehyde in a buffer solution at a pH of from 8 to 9.5 at a temperature within the range of from 5° to 30° C. and the reaction of bonding is effected for 30 to 120 minutes. After bonding of fibrinolysin with oxidized dextran the unreacted aldehyde groups of the carrier are easily converted into inert hydroxy groups under the action of a mild reducing agent such as sodium borohydride. The polysaccharide derivative of fibrinolysin is separated from the excess of mineral salts by demineralization on membranes, in particular, by dialysis against water. The solution of the resulting preparation is lyophilized. The desired product thus obtained is a yellowish powder having no taste or odor. The preparation is hygroscopic, readily soluble in water and 0.9% isotonic solution of sodium chloride, substantially insoluble in 95% ethanol, ether and chloroform. The specific activity of the preparation is 20 to 25 units/mg, the yield of the desired product is 25 to 30%.

The method of covalent bonding of fibrinolysin with oxidized dextran satisfies both clinical and technological requirements of the preparation of medical compounds: the matrix contains no toxic groups, the excessive reactive aldehyde groups, in order to avoid their reactions with proteins contained in the organism, are reduced to hydroxy groups. In the process the use is not made of highly toxic compounds; the preparation of activated dextran and subsequent binding of dialdehydedextran with fibrinolysin occurs under mild conditions in an aqueous medium; no use of organic solvents is required; the process conditions ensure a substantially complete bonding of fibrinolysin with the polymer, whereby the necessity of additional stages of separation of the non-bound protein from the bound one is avoided; consequently all stages of the preparation of the polysaccharide fibrinolysin derivative are simple and can be implemented under commercial conditions in the production of a medical compound—polysaccharide derivative of fibrinolysin.

For a better understanding of the present invention some specific examples illustrating the method of preparing a polysaccharide derivative of fibrinolysin are given hereinbelow.

EXAMPLE 1

1.25 g of dextran-polyglucin are dissolved in 25 ml og distilled water and mixed with 0.71 g of potassium periodate. Oxidation is carried out at the temperature of 22°±3° C. under continuous stirring for one hour.

The resulting solution of oxidized polyglucin is passed through a column packed with 6 g of anionite in the acetate form, the volume of the eluate equal to the dead volume of the column (3-5 ml) is discarded and the remaining 20 ml are collected into a metering cylinder. 20 ml of oxidized and purified polyglucin with the molecular mass of 20,000 is mixed with 110 ml of 0.2 M of soda buffer solution with the pH of 9.5 (to the concentration of oxidized polyglucin equal to 7.5 mg/ml) and 6.5 g of fibrinolysin are added thereto under mild stirring.

The reaction mixture in the amount of 130 ml is kept at pH of 8.4-8.9 at the temperature of 20°±3° C. for one hour, then cooled to 10°±5° C. and combined with 40 ml of 0.5% solution of sodium borohydride. The reduction reaction occurs at pH of 8.5-9.0 for 30 minutes.

The solution of the polysaccharide derivative of fibrinolysin is poured into cellophane bags—two by 85 ml—and subjected to dialysis at the temperature of 6°±2° C. against 17 l of distilled water for 24 hours. The dialyzed solution of the polysaccharide derivative of fibrinolysin is diluted with apyrogenic water to 350 ml, passed through a sterile filter (pore diameter 0.22 μm) and lyophilically dried.

The yield of the preparation is 2,275 mg. The specific fibrinolytic activity is 21.2 units/mg of the preparation having total activity of 48.230 units which is 31.0% of the initial value. The thus-obtained product is a yellowish powder having no taste and odor. The preparation is hygroscopic, soluble in water and 0.9% isotonic solution of sodium chloride, substantially insoluble in 95% ethanol, ether and chloroform.

EXAMPLE 2

10 g of dextran-polyglucin are dissolved in 200 ml of distilled water and mixed with 5.65 g of potassium periodate. Oxidation is carried out at the temperature of 20°±3° C. under continuous stirring for 1 hour. The resulting solution of oxidized polyglucin with the molecular mass of 110,000 and the oxidation degree of 20±2% is passed through a glass column packed with 50 g of an anionite in its acetate form to fully separate the oxidized polyglucin from anions HCOO, $IO_4^-$, $HCO_3^-$. At the outlet from the column the eluate in the amount equal to the dead volume of the column is discarded (50 ml) and 150 ml of the solution containing oxidized polyglucin in the concentration of 50 mg/ml are collected into a metering cylinder.

150 ml of the purified solution of oxidized polyglucin are mixed with 425 ml of 0.2 M soda buffer solution having pH 9.5. The resulting solution of oxidized polyglucin is mixed with the solution of native fibrinolysin prepared by dissolution of 45 g of fibrinolysin in 425 ml of distilled water.

The reaction mixture in the volume of 1,000 ml is kept at the temperature of 20°±3° C. for 40 minutes and combined with 310 ml of 0.5% solution of sodium borohydride cooled to the temperature of 6°±2° C. The reduction reaction proceeds over 30 minutes. Then the solution of the polysaccharide derivative of fibrinolysin is subjected to dialysis against distilled water in the ratio of the dialyzed solution to distilled water of 1:150 respectively for 24 hours at a temperature of 4°–7° C. and lyophylically dried. The yield of the preparation is 12.5 g its specific activity is 24 units/mg and the total activity—300,000 units which is 30% of the initial value.

The resulting product comprises a yellowish powder having no taste and odor. The preparation is hygroscopic, readily soluble in water and 0.9% of isotonic solution of sodium chloride, substantially insoluble in 95% ethanol, ether, cloroform.

EXAMPLE 3

The solution of 2 g of dextran dialdehyde with the molecular mass of 50,000 in 40 ml of distilled water is mixed with 200 ml of 0.2 M soda buffer (pH 9.5) and 13 g of fibrinolysin are added to the solution under stirring. The reaction mixture is kept at pH 9.5 for one hour at the temperature of 5° C., then combined with a cooled solution of sodium borohydride (0.5% solution, 100 ml) in soda buffer having a pH of 8.5. The reduction reaction is effected for 30 minutes at the temperature of 4° C. and pH of 8.5–9.0.

The solution of the polysaccharide derivative of fibrinolysin is poured into cellophane bags and subjected to dialysis against distilled water at the temperature of 4°±2° C. for 24 hours. The dialyzed solution of the polysaccharide derivative of fibrinolysin diluted with apyrogenic water to 700 ml is passed through a sterile filter (pore diameter 0.22 μm) and lyophilically dried.

The yield of the preparation is 4.500 mg. The resulting product comprises a yellowish powder without any odor and taste. The specific fibrinolytic activity of the preparation is equal to 20 units/mg; the total activity is 90,000 units which is equal to 30% of the initial value.

What is claimed is:

1. A method of preparing a polysaccharide derivative of fibrinolysin having thrombolytic activity comprising reacting fibrinolysin with dextran dialdehyde having a molecular mass of from 20,000 to 110,000 at a pH of 8.0 to 9.5 and at a temperature within the range of from 5° to 30° C. to form a covalent bond, reducing the resulting polysaccharide derivative of fibrinolysin with sodium borohydride and isolating the product.

2. A method as claimed in claim 1, wherein sodium borohydride is used in a ratio to the polysaccharide derivative of fibrinolysin equal to 1.5–2.0:1.

3. A polysaccharide derivative of fibrinolysin having thrombolytic activity obtained by the steps comprising reacting fibrinolysin with dextran dialdehyde having a molecular mass of from 20,000 to 110,000 at a pH of 8.0 to 9.5 and at a temperature within the range of from 5° to 30° C. to form a covalent bond, reducing the resulting polysaccharide derivative of fibrinolysin with sodium borohydride and isolating the product.

4. The polysaccharide derivative of fibrinolysin prepared according to claim 1 which is water soluble.

5. A polysaccharide derivative of fibrinolysin which is water soluble and has prolonged thrombolytic activity, obtained by reacting fibrinolysin with dextran dialdehyde to form a covalent bond and reducing the product, said derivative being represented as follows:

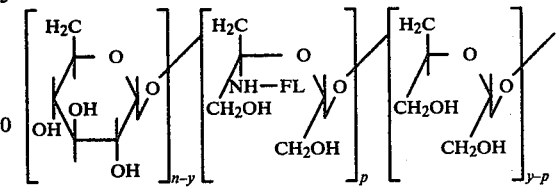

wherein
FL is fibrinolysin
n is 100 mol % of glucopyranose units of dextran
y is 10–25 mol % of oxidized glucopyranose units of dextran
p is the molar percentage of $NH_2$ groups of fibrinolysin bonded to dextran, and
wherein the content of fibrinolysin is 10 to 30 mol % and the content of dextran 90 to 70 mol %.

* * * * *